(12) United States Patent
Garrison et al.

(10) Patent No.: US 11,213,656 B2
(45) Date of Patent: Jan. 4, 2022

(54) MEDICAL DEVICE WITH ANTI-ROTATION PUSH TAB

(71) Applicant: Becton, Dickinson and Company, Franklin Lakes, NJ (US)

(72) Inventors: Michael Garrison, La Jolla, CA (US); Bart D. Peterson, Farmington, UT (US); Ralph L. Sonderegger, Farmington, UT (US); Jonathan Karl Burkholz, Salt Lake City, UT (US); Thomas Solosko, Draper, UT (US); Stephen Bornhoft, Raynham, MA (US); Marty Stout, South Jordan, UT (US); Carl Ellis, Tucson, AZ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 156 days.

(21) Appl. No.: 16/570,713

(22) Filed: Sep. 13, 2019

(65) Prior Publication Data

US 2020/0001050 A1 Jan. 2, 2020

Related U.S. Application Data

(63) Continuation-in-part of application No. 15/467,929, filed on Mar. 23, 2017, now Pat. No. 10,737,059.

(Continued)

(51) Int. Cl.
*A61M 25/06* (2006.01)
*A61M 25/00* (2006.01)
*A61M 5/158* (2006.01)

(52) U.S. Cl.
CPC .... *A61M 25/0612* (2013.01); *A61M 25/0097* (2013.01); *A61M 25/0606* (2013.01);

(Continued)

(58) Field of Classification Search
CPC .......... A61M 25/0612; A61M 25/0606; A61M 25/0693; A61M 25/0097; A61M 5/158; A61M 2025/006
See application file for complete search history.

(56) References Cited

U.S. PATENT DOCUMENTS

| | | |
|---|---|---|
| 4,191,186 A | 3/1980 | Keeler |
| 4,863,432 A | 9/1989 | Kvalo |

(Continued)

FOREIGN PATENT DOCUMENTS

| | | |
|---|---|---|
| EP | 747087 | 12/1996 |
| WO | 2013/137348 | 9/2013 |

*Primary Examiner* — Bradley J Osinski
(74) *Attorney, Agent, or Firm* — Kirton McConkie; Whitney Blair; Kevin Stinger

(57) ABSTRACT

A catheter system may include a catheter hub, a septum disposed within the catheter hub, a catheter tube extending from the catheter hub, a needle hub, and an introducer needle secured within the needle hub. The catheter hub may include a push tab and one or more ribs, which may extend outwardly from an upper surface of the catheter hub. The ribs may be shorter in height than the push tab and/or may be generally parallel to the push tab. The introducer needle may include a flashback notch. In response to insertion of the introducer needle into vasculature, blood may flow into the introducer needle, through the flashback notch, and into a flashback chamber disposed between the septum and the catheter tube. The flashback chamber may be disposed distal to the push tab and the ribs, which may improve visualization of the flashback chamber by a user.

20 Claims, 19 Drawing Sheets

Related U.S. Application Data

(60) Provisional application No. 62/323,525, filed on Apr. 15, 2016.

(52) U.S. Cl.
CPC ......... *A61M 25/0693* (2013.01); *A61M 5/158* (2013.01); *A61M 2025/006* (2013.01)

(56) References Cited

U.S. PATENT DOCUMENTS

| | | | |
|---|---|---|---|
| 4,964,854 A | 10/1990 | Luther | |
| 5,000,740 A * | 3/1991 | Ducharme | A61M 25/0631 604/162 |
| 5,215,528 A | 6/1993 | Purdy et al. | |
| 5,501,675 A | 3/1996 | Erskine | |
| 5,676,656 A | 10/1997 | Brimhall | |
| 5,713,876 A | 3/1998 | Bogert et al. | |
| 5,913,846 A | 6/1999 | Szabo | |
| 5,951,515 A | 9/1999 | Osterlind | |
| 6,004,294 A | 12/1999 | Brimhall et al. | |
| 6,616,630 B1 * | 9/2003 | Woehr | A61M 5/3273 604/110 |
| 6,638,252 B2 | 10/2003 | Moulton et al. | |
| 6,749,588 B1 | 6/2004 | Howell et al. | |
| 6,953,448 B2 | 10/2005 | Moulton et al. | |
| 7,530,965 B2 | 5/2009 | Villa et al. | |
| 7,691,093 B2 * | 4/2010 | Brimhall | A61M 25/0693 604/506 |
| 7,722,569 B2 | 5/2010 | Soderholm et al. | |
| 8,206,355 B2 | 6/2012 | Thorne | |
| 9,056,188 B2 | 6/2015 | Hager et al. | |
| 9,095,679 B2 | 8/2015 | Nishimura et al. | |
| 2002/0177812 A1 | 11/2002 | Moulton et al. | |
| 2003/0060760 A1 | 3/2003 | Botich | |
| 2006/0270991 A1 | 11/2006 | Adams | |
| 2008/0140011 A1 | 6/2008 | Hager | |
| 2009/0105689 A1 * | 4/2009 | Mitchum | A61M 25/0097 604/523 |
| 2010/0106092 A1 | 4/2010 | Tanabe et al. | |
| 2010/0249713 A1 | 9/2010 | Burkholz | |
| 2011/0054403 A1 | 3/2011 | Tanabe et al. | |
| 2014/0025044 A1 | 1/2014 | Zamarripa et al. | |
| 2014/0303561 A1 | 10/2014 | Li | |
| 2014/0364809 A1 | 12/2014 | Isaacson et al. | |
| 2015/0238733 A1 | 8/2015 | Abdulla | |
| 2017/0120009 A1 | 5/2017 | Garrison et al. | |

* cited by examiner

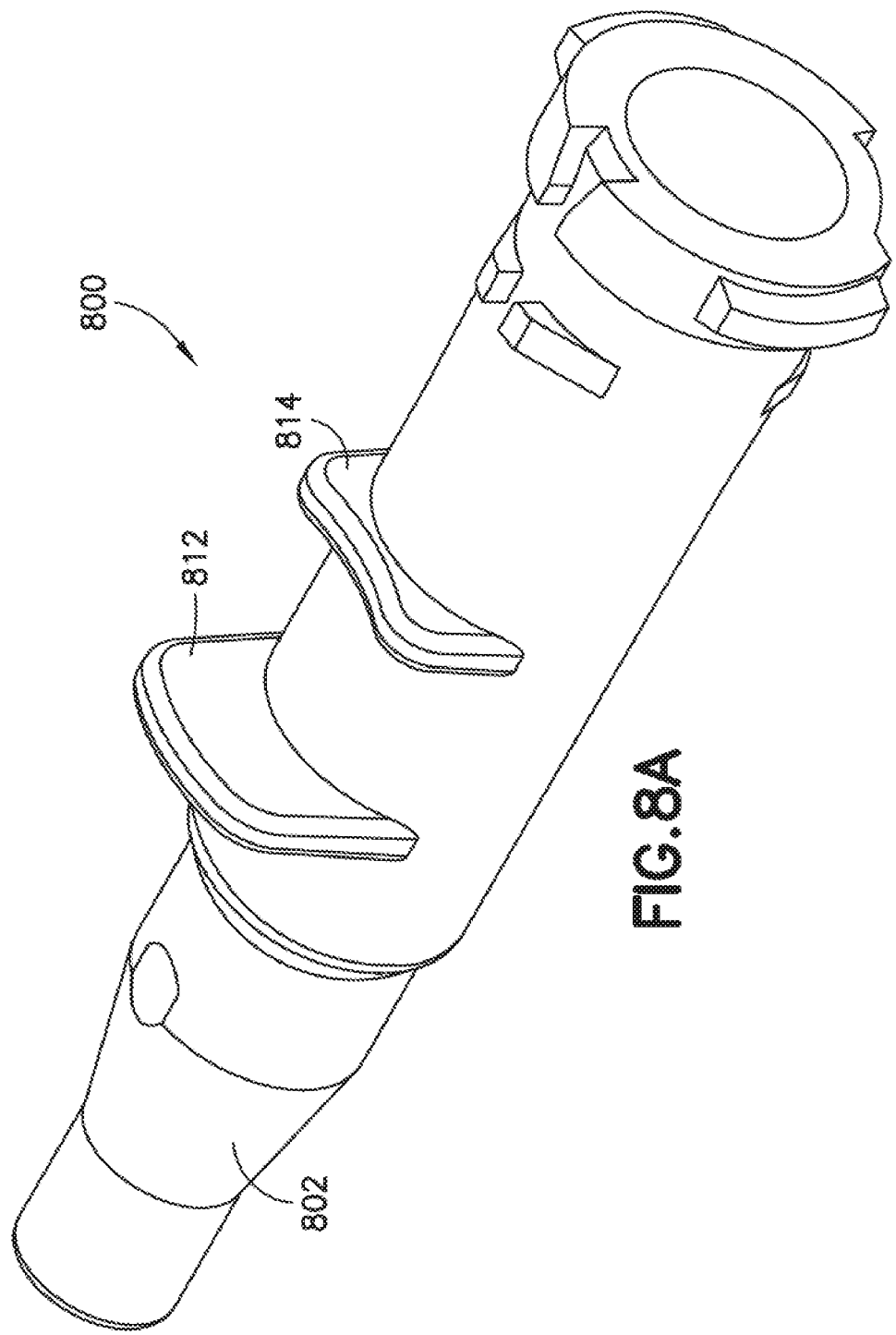

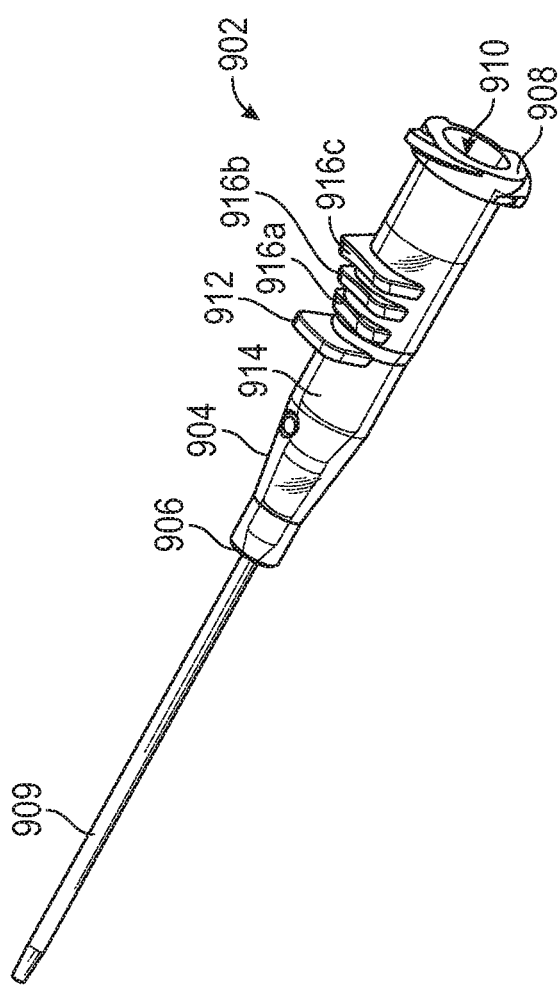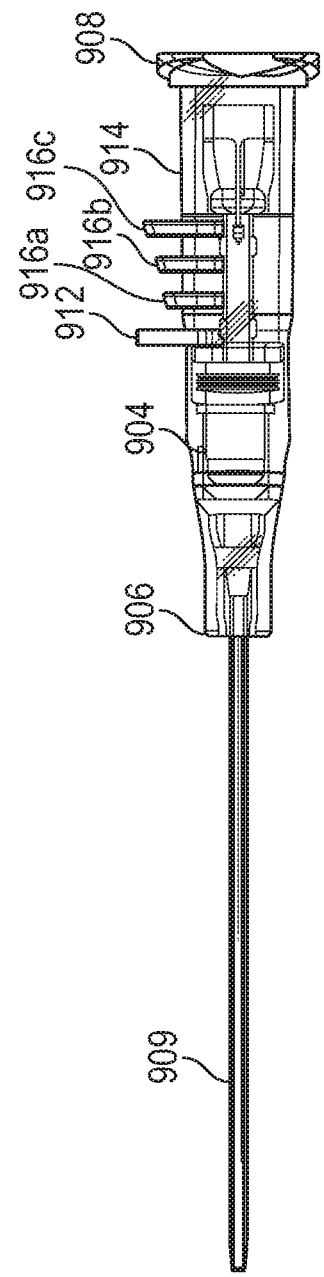
FIG. 10A
FIG. 10B

MEDICAL DEVICE WITH ANTI-ROTATION PUSH TAB

CROSS-REFERENCE TO RELATED APPLICATION

This application is a continuation-in-part of U.S. patent application Ser. No. 15/467,929, filed Mar. 23, 2017, titled "MEDICAL DEVICE WITH ANTI-ROTATION PUSH TAB," which claims priority to U.S. Provisional Patent Application No. 62/323,525, filed Apr. 15, 2016, titled "CATHETER HUB WITH ANTI-ROTATION PUSH TAB," which are hereby incorporated by reference in their entirety.

FIELD OF THE INVENTION

The present invention relates, in general, to an anti-rotation push tab for a medical device. More specifically, the anti-rotation push tab is especially adapted for use with intravenous catheters, as well as catheter introducers and guidewire introducers.

BACKGROUND OF THE INVENTION

An intravenous (IV) catheter is typically mounted over an introducer needle having a sharp distal tip in order to properly insert an IV catheter into a patient. At least the distal portion of the catheter tightly engages the outer surface of the needle to facilitate insertion of the catheter into the blood vessel. The distal tip of the needle preferably extends beyond the distal tip of the catheter.

Although typical IV catheter and introducer needle assemblies generally perform their functions satisfactorily, they do have certain drawbacks. Some PIVCs have issues with stability of the catheter hub when advancing it and are prone to free spinning on the insertion needle during the insertion process. Oftentimes, the catheter hub includes a push tab to aid in advancing the catheter hub. As the catheter hub advances, in some cases, it experiences rolling where the catheter hub spins along the axis of the insertion needle. This can cause a problem when the push tab rotates out of reach of the finger being used to advance the catheter hub.

In some cases an edge is provided on the catheter hub so that the user can advance the catheter hub regardless of its angular position. There is a concern in that the edge becomes quite uncomfortable to a patient when the catheter hub has been taped down at the insertion site thus forcing the edge against the patient's soft tissue.

SUMMARY OF EMBODIMENTS OF THE INVENTION

Accordingly, it is an aspect of the present invention to provide features that oppose the rotational movement of a medical device in relation to the user's finger. In the case of an IV catheter, this can enhance the stability of the catheter during insertion, hooding, and threading. Embodiments of the present invention provide a platform that pushes on the user's finger when the catheter begins to rotate and allows the user's finger to resist the rotation and also steer the catheter back to the neutral starting position. Free spinning of the catheter hub can be prevented without making any other design compromises or increasing the cost of the design.

The foregoing and/or other aspects of the present invention are achieved by a medical device, comprising a hub or housing having a push tab including a main portion extending radially from an upper surface of the hub or housing, and at least one anti-rotation feature for resisting rotation of the hub or housing. A cannula is directly or indirectly connected to the hub or housing. The medical device may be a catheter, the cannula may be a catheter tube, and the hub or housing may be a catheter hub or an introducer needle tip shield for the catheter.

The foregoing and/or other aspects of the present invention are also achieved by a medical device, comprising a housing having a push tab including a main portion extending radially from an upper surface of the housing, and at least one anti-rotation feature for resisting rotation of the housing, and a cannula connected to the housing.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which:

FIGS. 8A and 8B illustrate a catheter hub incorporating an anti-rotation push tab according to yet another embodiment of the invention;

FIG. 10A is an upper perspective view of another catheter hub, according to some embodiments;

FIG. 10B is a side view of the catheter hub of FIG. 10A, according to some embodiments;

DETAILED DESCRIPTION OF EMBODIMENTS OF THE PRESENT INVENTION

Figure 1:
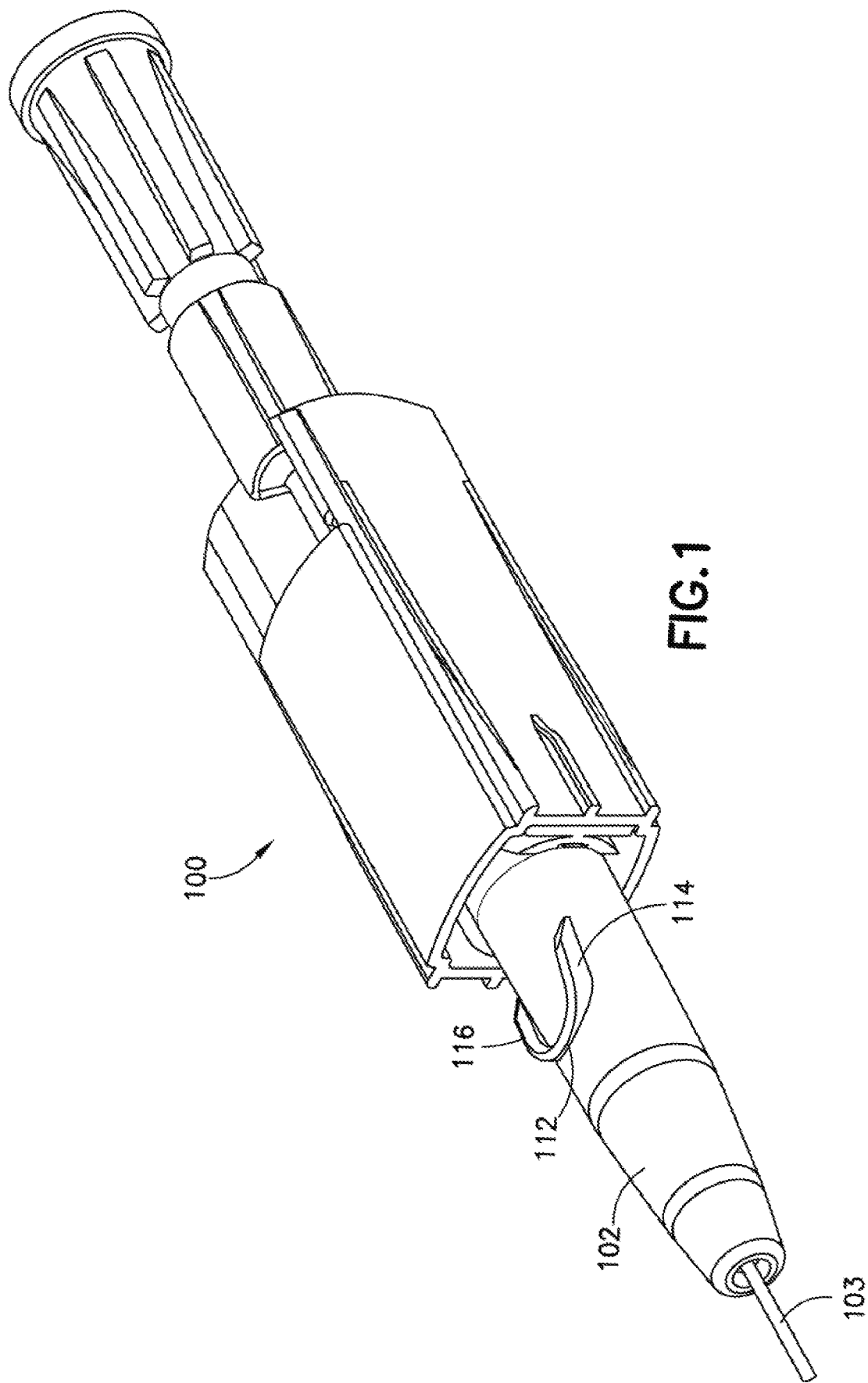
FIG. 1 illustrates a catheter hub incorporating an anti-rotation push tab.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

Referring in more specific detail to FIG. 1 of the drawings, there is illustrated a medical device such as a safety IV catheter assembly 100 incorporating a catheter hub (hub) 102 and a flexible tube or cannula 103. The catheter hub 102 is releasably engaged to a needle tip shield 118 (housing). The catheter tube 103 is directly or indirectly connected to the hub 102 or housing 118. The material of the catheter tube 103 may consist of, for example, polyurethane (PU), FEP or PTFE (Teflon™). For purposes of illustration, the catheter hub 102 is shown attached to an introducer needle hub 120 prior to insertion. The catheter hub 102 includes a push tab 112 and anti-rotation features in the form of extension members 114 and 116. A user can engage the push tab 112 to advance the catheter hub 102 forward thereby advancing the catheter. As illustrated in FIG. 1, the push tab 112 extends radially from an upper surface of the catheter hub 102. The first extension 114 extends from a first side of the push tab 112 around the side of the upper surface of the catheter hub 102 and the second extension 116 extends from a second side of the push tab 112 around the other side of the upper surface of the catheter hub 102. The first extension 114 and the second extension 116 act as anti-rotation members that counteract rotation of the catheter hub 102. The push tab and first and second extensions together form a substantially C-shape when viewed from above.

The push tab and first and second extensions are shaped and configured to cradle a user's finger as the push tab 112 is advanced forward. The first extension 114 and second extension 116 resist angular rotation of the catheter hub 102 relative to the user's finger and enhance stability during insertion.

In an alternate embodiment (not shown), the push tab 112 and extension members 114, 116 are similarly disposed on a top distal surface of the needle tip shield 118, instead of on the catheter hub 102. The introducer needle hub 120 includes an opening at a top distal surface to allow the push tab 112 and extension members 114, 116 of the needle tip shield 118 to extend upwardly and be accessible to the user. The catheter tube 103 is directly or indirectly connected to the hub 102 or housing 118. Accordingly, the user can engage the push tab 112 on the needle tip shield 118 to advance the catheter hub 102 and catheter forward. After the catheter is inserted, the introducer needle hub 120 is used to withdrawn the introducer needle of the catheter assembly 100 from the catheter tube 103 and the catheter hub 102. Subsequently, a distal end of the introducer needle is retracted and enclosed in the needle tip shield 118. The push tab 112 and extension members 114, 116 of the needle tip shield 118 also aid the user to withdraw the introducer needle of the catheter assembly 100.

For this and other subsequently-described embodiments, all reference characters designating corresponding parts of the embodiments will be the same as in the embodiment of FIG. 1, except that they will be in a different series, for example, in the 200 series, or the 300 series. The differences of the second and third embodiments with respect to the first embodiment will now be described.

Figure 2:
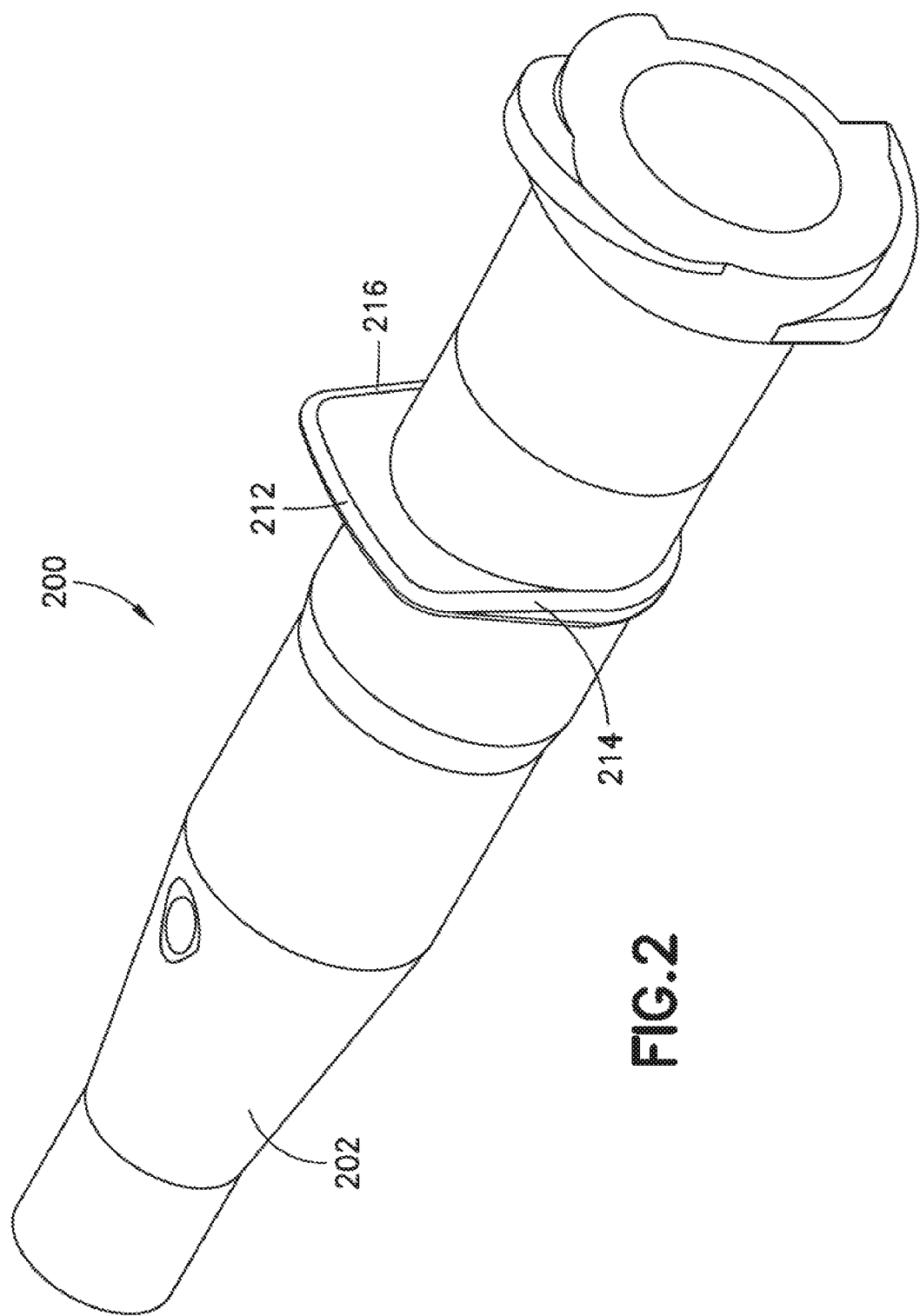
FIG. 2 illustrates a catheter hub incorporating a sculpted anti-rotation push tab.

FIG. 2 depicts a push tab 212 formed on an upper surface of a catheter hub 202 for a catheter hub 200. As illustrated in FIG. 2, the push tab 212 is a wall-like formation extending radially from an upper surface of the catheter hub 202. The push tab 212 includes a raised and sculpted configuration where a distal side of the wall-like main portion 212 is concave so as to conform to the curvature of the user's finger and allow the user to control rotation. A first extension 214 extends from a first side of the wall-like main portion 212 around an outer surface of the catheter hub 202, and a second extension 216 extends from a second side of the main portion 212 around the outer surface of the catheter hub 202. The first extension 214 and the second extension 216 act as anti-rotation members that counteract rotation of the catheter hub 202. The sculpted configuration of the push tab 212 provides a tactile feel for the user with regard to placement of the user's finger.

Figure 3:
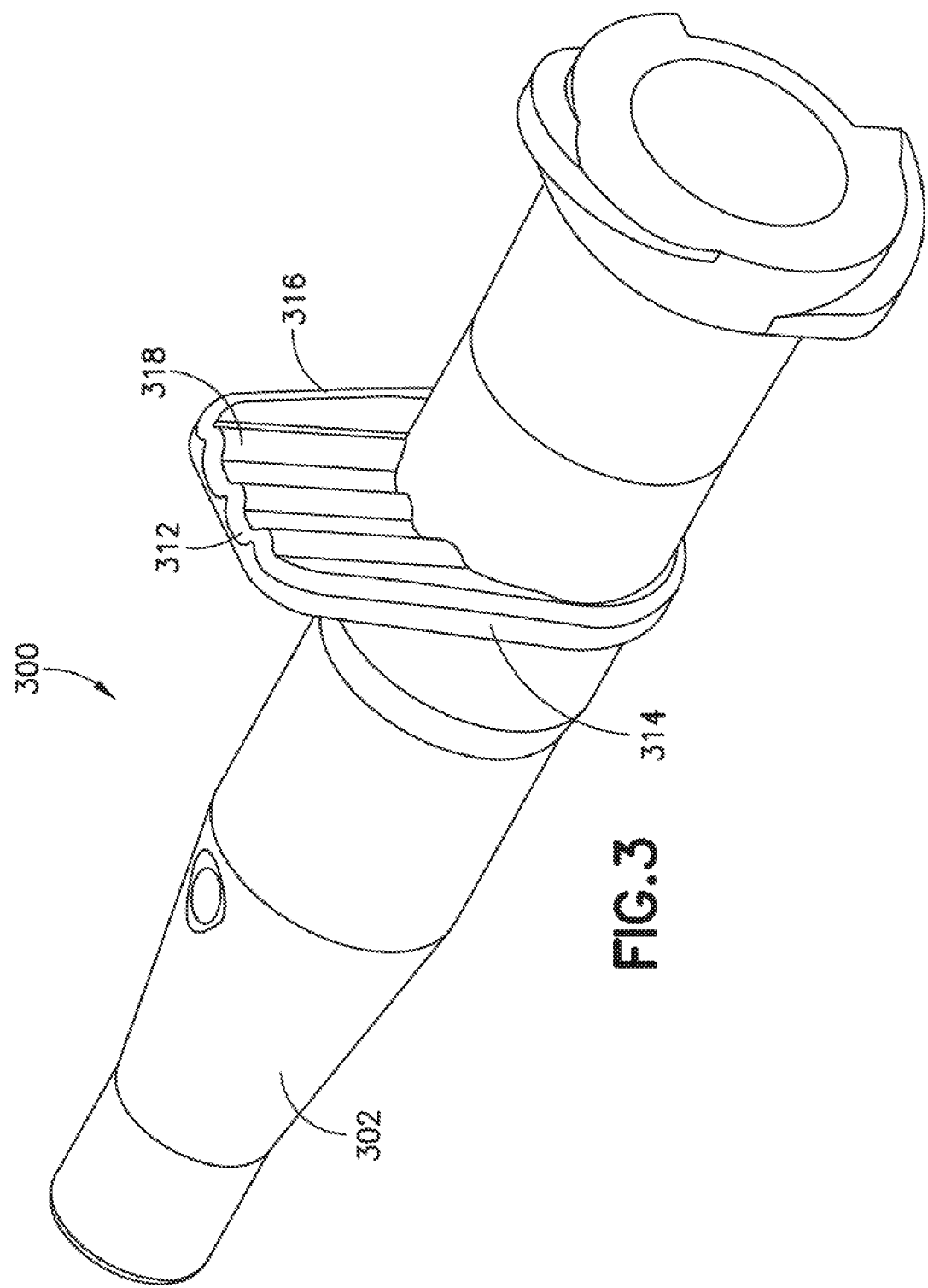
FIG. 3 illustrates a catheter hub incorporating a sculpted anti-rotation push tab including ribs.

FIG. 3 provides a sculpted push tab 312 on an upper surface of a catheter hub 302. The push tab 312 includes ribs 318 disposed on a wall-like main portion of the tab 312. Ribs 318 enhance the tactile feel with regard to placement of the user's finger and assist in maintaining the user's finger on the tab 310.

Figure 4:
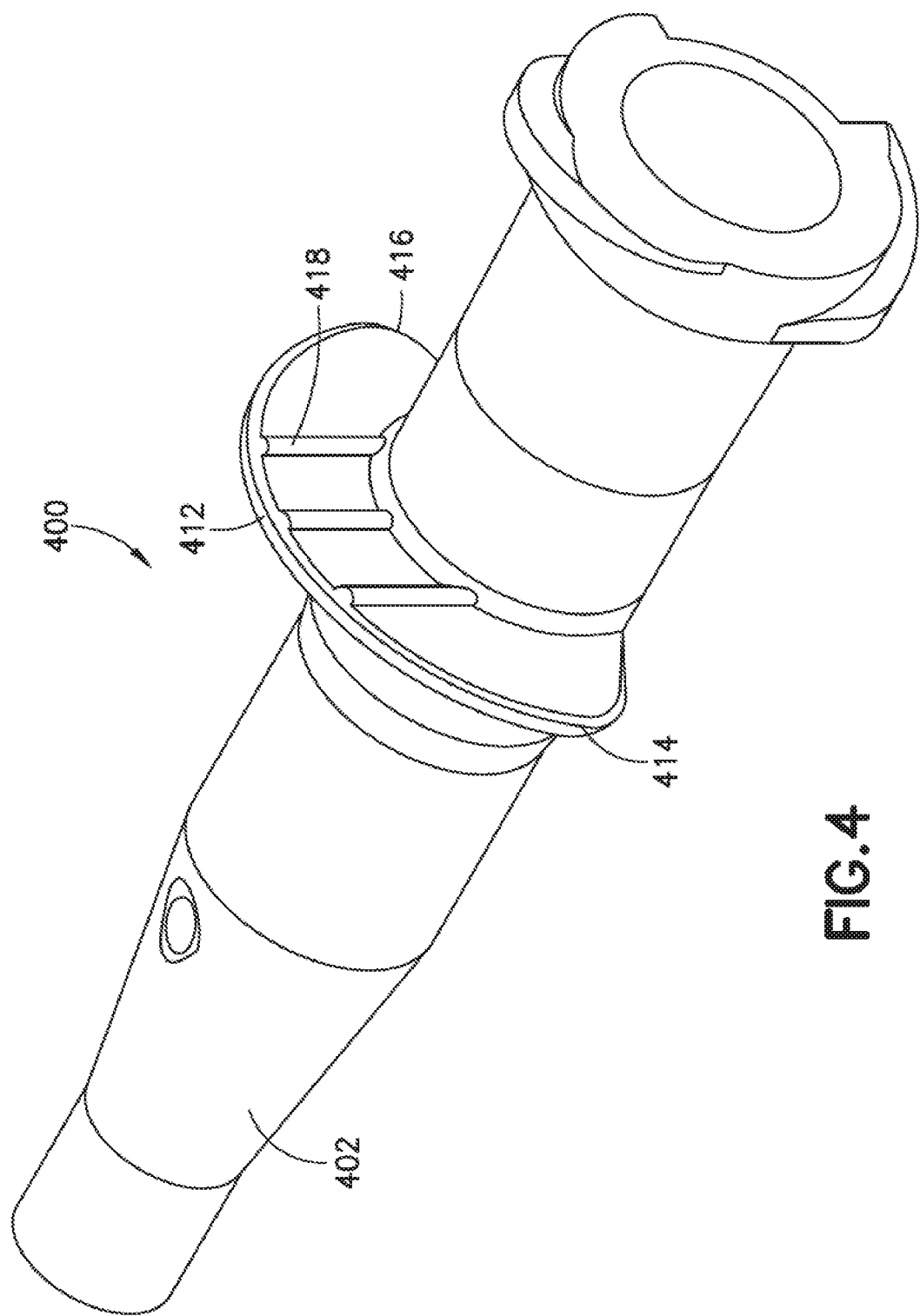
FIG. 4 illustrates a catheter hub incorporating an extended anti-rotation push tab.

A push tab 412 is formed on an upper surface of the catheter hub 402 illustrated in FIG. 4 for use with a catheter. The push tab 412 includes a wall-like main portion extending radially from an upper surface of the catheter hub 402. The push tab 412 also includes a first extension 414 and a second extension 416. The first extension 414 and second extension 416 both extend radially from side surfaces of the catheter hub. Together with the main portion 412, they provide a larger circumference for the finger-engaging surface than the embodiments of FIGS. 2 and 3. At least one rib 418 is formed on the push tab 412 to facilitate engagement with a user's finger and prevent rotation. The first and second extension 414 and 416 limit rotation of the catheter hub 402 such that as the catheter rotates either clockwise or counterclockwise, either the first extension 414 or the second extension 416 will contact the skin of the patient and prevent further rotation, while the push tab 412 is still in contact with the clinician's finger, allowing advancement.

Figure 5:
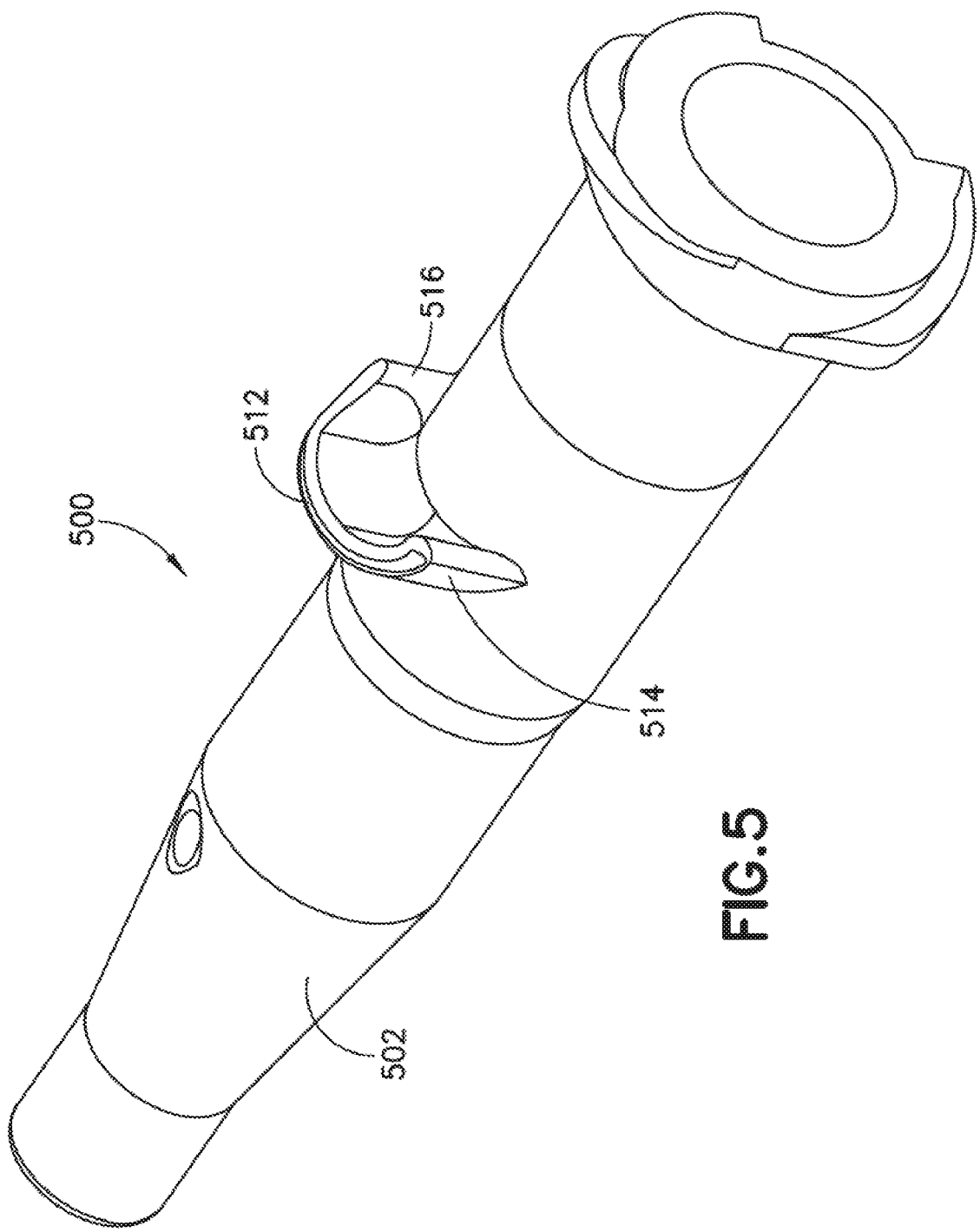
FIG. 5 illustrates a catheter hub incorporating a deep sculpted anti-rotation push tab.

FIG. 5 illustrates a catheter hub 502 with a more deeply sculpted push tab 512 formed on an upper surface of the catheter hub 502. The deep-sculpted push tab 512 includes a wall-like main portion extending radially from an upper surface of the catheter hub 502. A first extension 514 and a second extension 516 extend from the wall-like main portion of the push tab 512. The first extension 514 and second extension 516 both extend proximally on the catheter hub 502 and curve toward the main portion of the push tab 512 to cradle a user's finger by engaging the sides of the clinician's fingers and allow the user to control lateral motion and rotation. The first extension 514 and the second extension 516 act as anti-rotation members that counteract rotation of the catheter hub 502.

Figure 6:
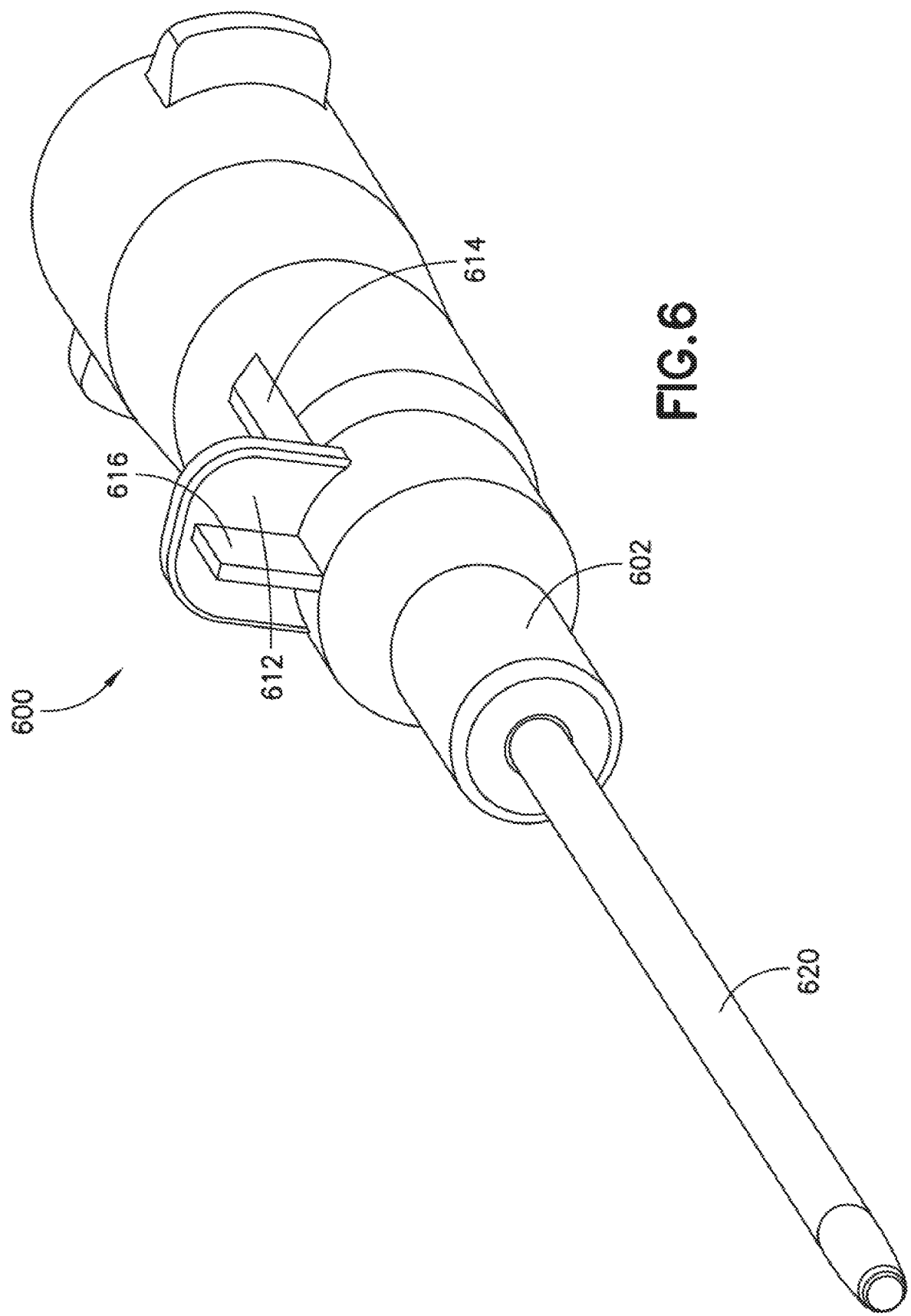
FIG. 6 illustrates a catheter hub incorporating an anti-rotation push tab according to another embodiment of the invention.

Regarding FIG. 6, a catheter hub 602 incorporating a catheter 620 is illustrated. A push tab 612 is formed on an upper surface of the catheter hub 602. As illustrated in FIG. 6, the push tab 612 is configured as a wall-like main portion extending radially from an upper surface of the catheter hub 602. A first cradling tab 614 extends from a first side of the push tab 612 perpendicular to a plane of the push tab 612. A second cradling tab 616 extends from a second side of the main portion 612 perpendicular to a plane of the push tab 612. The push tab 612, first extension 614 and second extension 616 thereby form a cradle shape to resist catheter hub rotation where the first extension 214 and the second extension 216 act as anti-rotation members that counteract rotation of the catheter hub 202.

Figure 7:
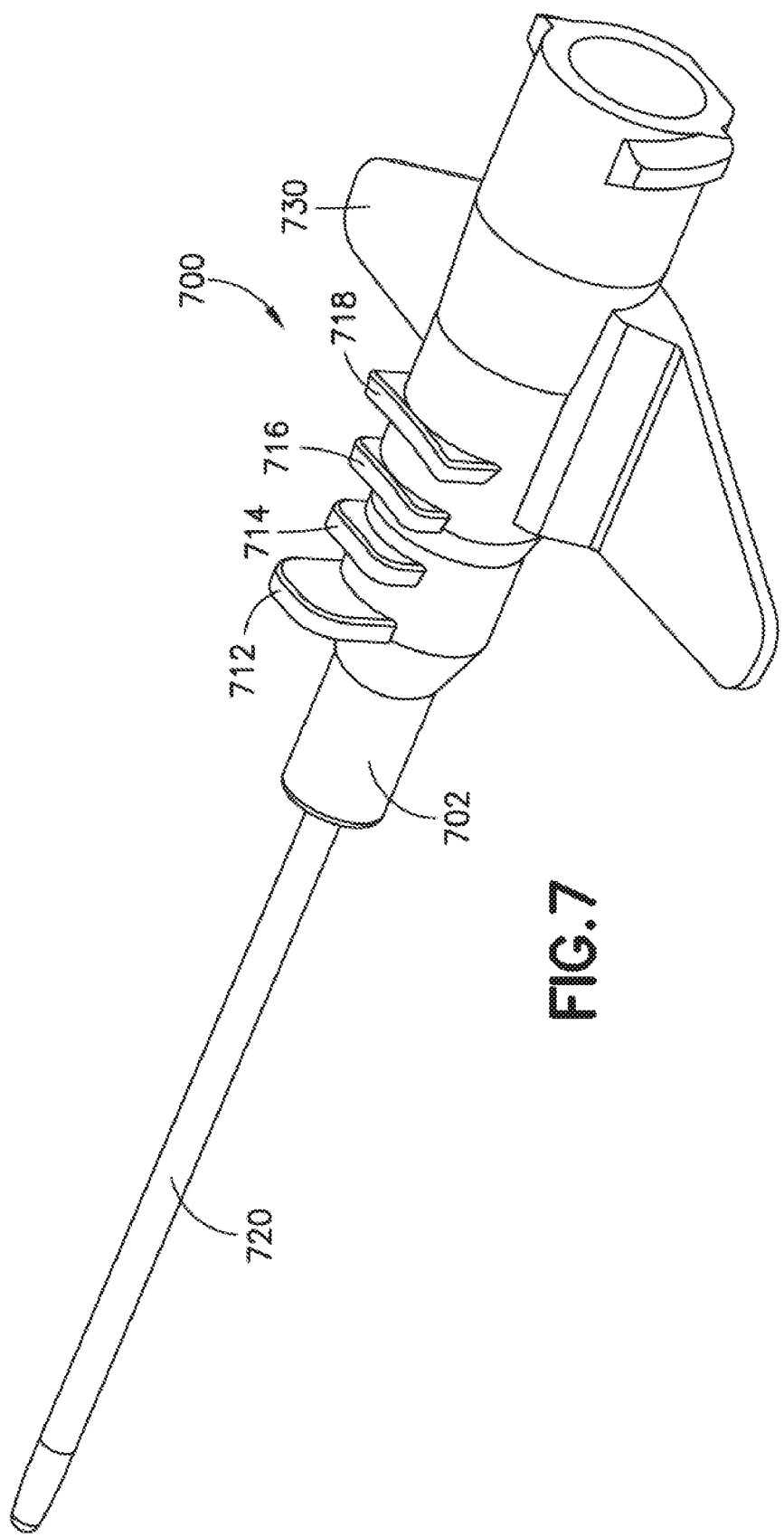
FIG. 7 illustrates a catheter hub incorporating an anti-rotation push tab according to still another embodiment of the invention.

FIG. 7 illustrates a wing catheter hub 702 incorporating a flexible IV catheter 720 and wings 730. An push tab 712 is formed on an upper surface of the catheter hub 702. As illustrated in FIG. 7, the push tab 712 includes a tall wall-like main portion extending radially from an upper surface of the catheter hub 702. Anti-rotation push tab 712 provides a cradling effect for the user's finger to aid insertion stability.

A first rib 714 parallel to the plane of the push tab 712, but shorter in height, extends from an upper surface of the catheter hub 702 and is spaced proximally from to the push tab 712. A second rib 716 and a third rib 718, also shorter in height than the first rib 714, may also extend from an upper surface of the catheter hub 702 parallel to the plane of the push tab 712. The ribs 714, 716, and 718 form a cradle shape to resist catheter hub rotation. Ribs 714, 716 and 718 also strengthen the catheter hub to prevent shrinkage which could cause leakage for any internal components of the catheter hub requiring a lengthwise seal.

Figure 8B:
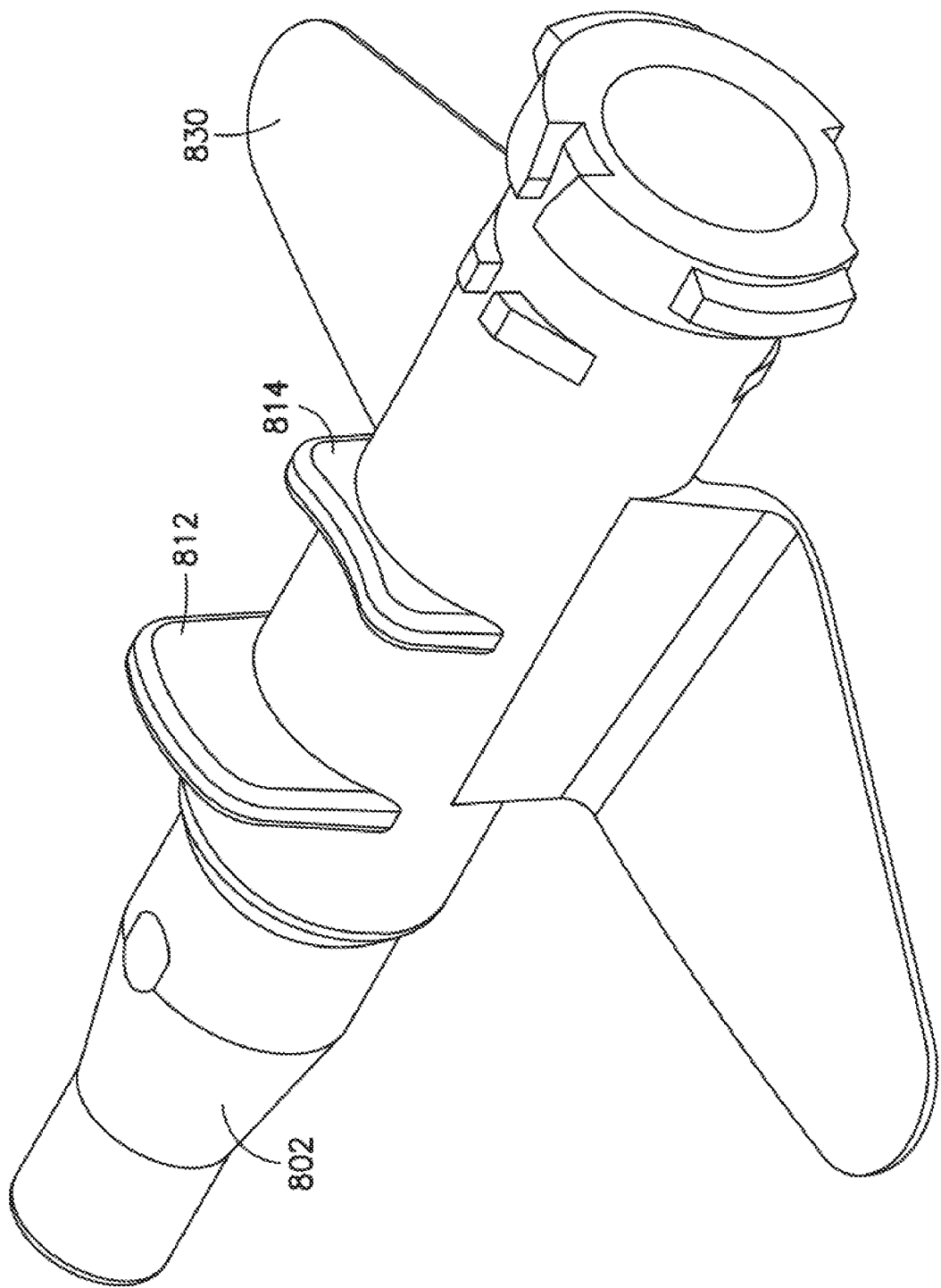

FIG. 7 illustrates three ribs 714, 716 and 718; however, a single rib 814 may be utilized to provide the necessary anti-rotational effect as illustrated in FIGS. 8A and 8B. The rib(s) 714, 716, 718 and 814 should be a distance from the push tab 712/812 where the rib is far enough from the push tab 712/812 to contact a user's advancing finger pad to provide stability but not so close that the finger pad does not contact the rib. The catheter hub 802 may be manufactured with or without wings 830 as shown in FIGS. 8B and 8A, respectively.

Referring now to FIGS. 9A-9H, a catheter system 900 may include a catheter assembly 902. In some embodiments, the catheter assembly 902 may include a catheter hub 904, which may include a distal end 906, a proximal end 908, a lumen 910 disposed between the distal end 906 and the proximal end 908. In some embodiments, a catheter tube 909 may extend distally from the distal end 906 of the catheter hub 904. In some embodiments, the catheter tube 909 may include an 18 to 24 gauge catheter tube or another suitable catheter tube. In some embodiments, the catheter tube 909 may be secured within the catheter hub 904 by a wedge or another suitable means. In some embodiments, the catheter system 900 may include a cap 911, which may be removed prior to insertion of the catheter system 900 into vasculature of a patient.

In some embodiments, the catheter hub 904 may include a push tab 912, which may extend outwardly from an upper surface 914 of the catheter hub 904. It should be understood that the embodiments of FIGS. 1-12 may be combined. For example, in some embodiments, the push tab 912 of FIGS. 9-12 may be similar or identical in terms of one or more included components and/or operation to one or more of the following: the push tab 112, the push tab 212, the push tab 312, the push tab 412, the push tab 512, the push tab 612, the push tab 712, and the push tab 812 described with respect to FIGS. 1-8. As another example, in some embodiments, the catheter hub 904 may include wings, illustrated, for example, in FIG. 8B. In some embodiments, the catheter hub 904 may not include wings.

In some embodiments, the catheter hub 904 may include one or more ribs 916, which may extend outwardly from the upper surface 914 of the catheter hub 904. In some embodiments, as illustrated, for example, in FIGS. 9A-9H, the catheter hub 904 may include a first rib 916a, a second rib 916b, and a third rib 916c (which may be referred to collectively in the present disclosure as "ribs 916"). In some embodiments, the catheter hub 904 may include more than three ribs 916. In some embodiments, the ribs 916 may be proximal to the push tab 912. In some embodiments, the second rib 916b may be proximal to the first rib 916a and/or the third rib 916c may be proximal to the second rib 916b. In some embodiments, the ribs 916 may be shorter in height than the push tab 912. In some embodiments, the ribs 916 may be a same height as each other. In some embodiments, the ribs 916 may be generally parallel to each other. In some embodiments, the ribs 916 may be generally perpendicular to a longitudinal axis 918 of the catheter tube 909. In some embodiments, the ribs 916 and the push tab 912 may be evenly spaced apart.

In some embodiments, the ribs 916 may form a cradle shape. In further detail, in some embodiments, a middle portion of each of the ribs 916 may be concave so as to conform to a curvature of the finger of the user. In some embodiments, the middle portion of each of the ribs 916 may be aligned with the longitudinal axis 918 of the catheter tube 909. In some embodiments, a configuration of the first rib 916a, the second rib 916b, and the third rib 916c may enhance stability during insertion of the catheter system 900 into the vasculature of the patient and may resist angular rotation of the catheter hub 904. In some embodiments, the first rib 916a, the second rib 916b, and the third rib 916c may cradle the finger of the user as the push tab 912 is advanced distally.

In some embodiments, the catheter system 900 may include a needle hub 920 and an introducer needle 922 extending distally from the needle hub 920. In some embodiments, the introducer needle 922 may include a sharp distal tip 924 and a proximal end 926. In some embodiments, the proximal end 926 may be secured within the needle hub 920.

Figure 9A:
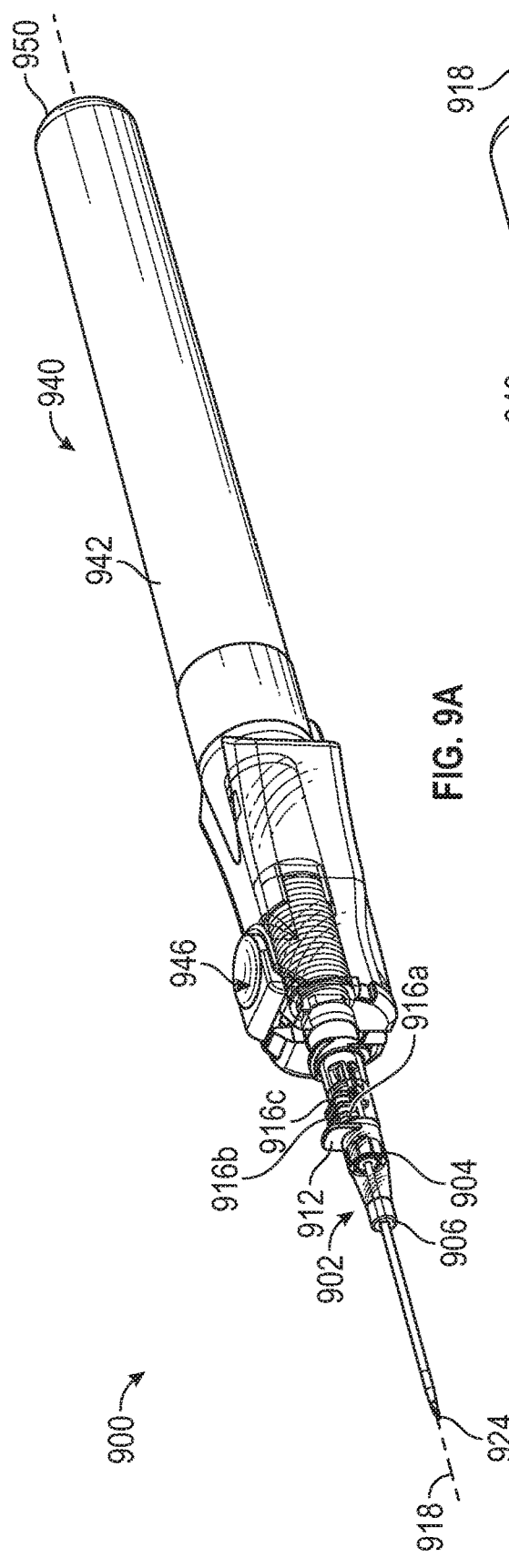
FIG. 9A is an upper perspective view of an example catheter system, according to some embodiments.

In some embodiments, a distal end 928 of the introducer needle 922 may include a flashback notch 930, which may extend through a wall of the introducer needle 922 proximate a lumen 932 within the introducer needle 922. In some embodiments, the notch 930 may include an opening, which may be generally round or another shape. In some embodiments, the introducer needle 922 may extend through the catheter tube 909 when the catheter system 900 is in an insertion configuration ready for insertion into the patient. FIG. 9A illustrates the catheter system 900 in the insertion configuration, according to some embodiments.

In some embodiments, a septum 934 may be disposed within the lumen 910 of the catheter hub 904. In some embodiments, the septum 934 may divide the lumen 910 of the catheter hub 904 into a distal chamber and a proximal chamber. In some embodiments, a septum actuator 935 may be configured to open the septum 934 in response to insertion of a medical device, such as an infusion device or a blood collection device, in the proximal end 908 of the catheter hub 906. In some embodiments, the distal chamber may correspond to a flashback chamber 929 configured to receive blood in response to insertion of the introducer needle 922 into the vasculature of the patient.

In some embodiments, the septum 934 may be constructed of silicon or another suitable material. In some embodiments, the septum 934 may include a single use septum. For example, in response to the septum 934 being opened by the actuator 935, the septum 934 may remain open. In some embodiments, the septum 934 may include a multi-use septum. In some embodiments, the actuator 935 may be coupled to a spring such that in response to the medical device being removed from the proximal end 908 of the catheter hub 906, the septum 934 may return to a closed position.

In some embodiments, the push tab 912 and/or the ribs 916 may be constructed of a rigid or semi-rigid material. In some embodiments, the push tab 912 and/or the ribs 916 may be constructed of a same material as the catheter hub 904. In these and other embodiments, the push tab 912 and/or the ribs 916 may be constructed of polypropylene, polyethylene, copolyester, polycarbonate, plastic, or another suitable material. In some embodiments, the push tab 912, the ribs 916, and the catheter hub 904 may be monolithically formed as a single unit. In some embodiments, the push tab 912 and/or the ribs 916 may be constructed of a soft or flexible material. For example, the push tab 912 and/or the ribs 916 may be constructed of a thermoplastic elastomer (TPE) or another suitable material.

In some embodiments, the catheter system 900 may be configured such that in response to insertion of the introducer needle 922 into the vasculature, blood flows proximally into the introducer needle 922 through the sharp distal tip 924. In some embodiments, blood may then flow proximally through the flashback notch into a space between an outer surface of the introducer needle 922 and an inner surface of the catheter tube 909. In some embodiments, blood may then flow proximally into the flashback chamber 929, which may be disposed between a distal face 936 of the septum 934 and a proximal end 938 of the catheter tube 909. In some embodiments, blood within the flashback chamber 929 may be visualized by the user and may indicate to the user that the introducer needle 922 is disposed within the vasculature. In some embodiments, the catheter hub 904 may be transparent or semitransparent, which may allow the user to visualize the blood within the flashback chamber 929.

In some embodiments, the flashback chamber 929 may be disposed distal to the ribs 916 and the push tab 912, which may improve visualization of the flashback chamber 929 by a user. In further detail, in some embodiments, the finger of the user may be stabilized on the push tab 912 and/or the ribs 916 during insertion of the catheter system 900 into the vasculature of the patient. In some embodiments, when the finger of the user is stabilized on the push tab 912 and/or the ribs 916, the user's view of the flashback chamber 929 may not be impeded by the finger due to the flashback chamber 929 being disposed distal to the ribs 916 and the push tab 912.

In some embodiments, the catheter system 900 may include a safety feature, which may shield the sharp distal tip 924 of the introducer needle 922 when the introducer needle 922 is withdrawn from the catheter hub 904. In some embodiments, the safety feature may be passive, such that no activation is required by the user, as will be discussed further with respect to FIG. 12. In some embodiments, the safety feature may include an active safety feature that is activated by the user.

In some embodiments, a safety feature 940 is an example of a possible active safety feature of the catheter system 900. In some embodiments, the safety feature 940 may include a barrel 942, a spring 944, an activation latch 946, and a projection 948. In some embodiments, the barrel 942 may include a proximal end 950 and a distal end 952. In some embodiments, the needle hub 920 may be slidably disposed in the barrel 942. In some embodiments, the barrel 942 may be generally hollow. In some embodiments, the spring 944 may be disposed about the introducer needle 922 and the needle hub 920.

In some embodiments, the activation latch 946 may include a top and a bottom and may be movably mounted adjacent to the distal end 952 of the barrel 942. In some embodiments, the activation latch 946 may be adapted for selective engagement with the needle hub 920 to hold the needle hub 920 adjacent to the distal end 952 of the barrel 942 against the bias of the spring 944 such that the introducer needle 922 extends beyond the distal end 952 of the barrel 942 and through the catheter tube 909 with the catheter hub 904 adjacent to the distal end 952 of the barrel 942. In some embodiments, the projection 948 may extend from the activation latch 946 for engagement with the catheter hub 904 to prevent movement of the activation latch 946 when the catheter hub 904 is adjacent to the distal end 952 of the barrel 942.

In some embodiments, the activation latch 946 may extend into the barrel 942 via a slot 954, which may be formed in barrel 942 adjacent to the distal end 952. In some embodiments, the activation latch 946 may include an opening 956, which may allow the introducer needle 922 and the needle hub 920 to extend through the activation latch 946. In some embodiments, the activation latch 946 may include the projection 948 that extends toward the distal end 906 of the catheter hub 904.

In some embodiments, when the activation latch 946 is "up" in a non-activated position, a smaller portion of the opening 956 is in communication with a lumen of the barrel 942. In this position, a smaller portion of the opening 956 may engage the needle hub 920 and holds needle hub 920 adjacent to the distal end 952 of barrel 942 against the force of the spring 944. In some embodiments, the needle hub 920 may include a generally hour-glass shape so that its medial portion has a smaller diameter than either end. This shape may facilitate engagement between the smaller portion of the opening 956 of the activation latch 946 and the needle hub 920.

In some embodiments, when the activation latch 946 is in the non-activated position, the projection 948 may be located inside the catheter hub 904. Thus, when the catheter tube 909 is still located on the introducer needle 922 with the catheter hub 904 adjacent to the distal end 952 of the barrel 942, the projection 948 may prevent the activation latch 946 from being moved "down" into an activated position. In some embodiments, a length of the projection 948 may be long enough so the projection 948 engages the catheter hub 904 when the catheter hub 904 is adjacent to the distal end 952 of the barrel 942. In some embodiments, the length of the projection 948 may not be so long that it interferes with use of the catheter tube 909 and the introducer needle 922.

In some embodiments, when the catheter tube 909 is moved off the introducer needle 922 so the catheter hub 904 is not adjacent to the distal end 952 of the barrel 942, the activation latch 946 can be moved "down," i.e. activated, because the catheter hub 904 no longer interferes with the movement of the projection 948. In this position, a larger portion of the opening 956 no longer engages the needle hub 920. In some embodiments, the larger portion of the opening 956 may be larger than a maximum diameter of the needle hub 920. In some embodiments, the spring 944 can thus force the needle hub 920 to the proximal end 950 of the barrel 942 and withdraw the sharp distal tip 924 of the introducer needle 922 into the barrel 942.

Figure 9B:
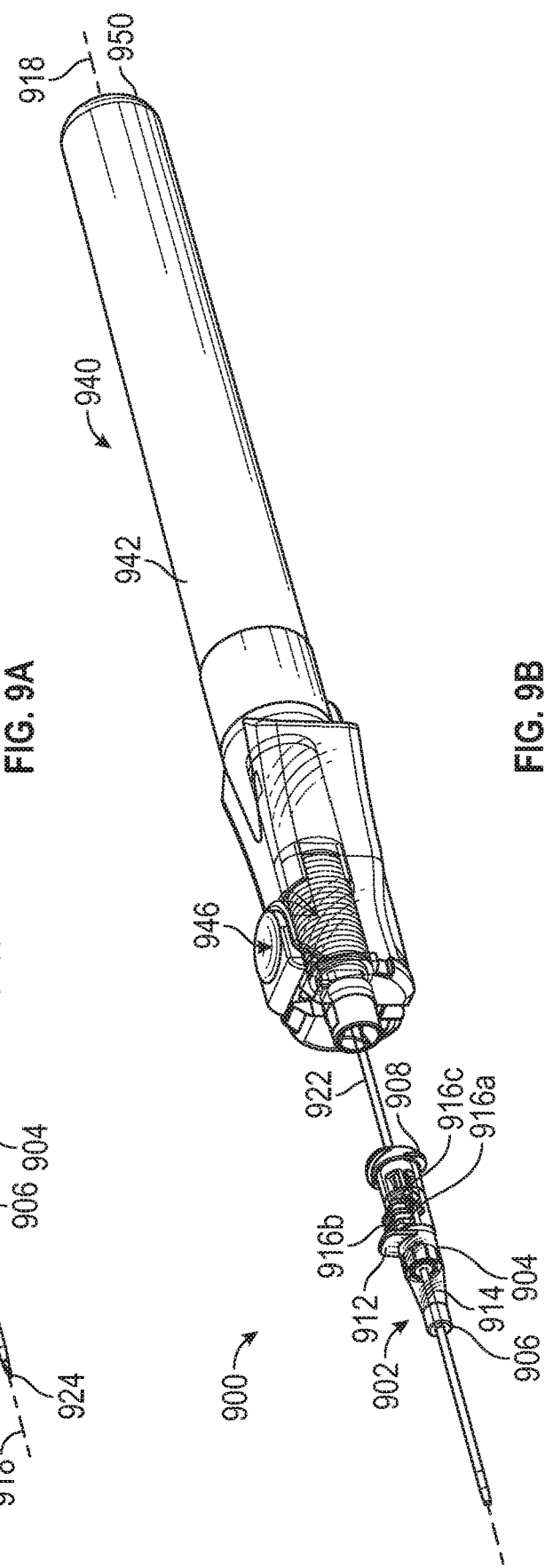
FIG. 9B is an upper perspective view of the catheter system of FIG. 9A, illustrating an example catheter hub advanced distally with respect to an example needle hub, according to some embodiments.
Figure 9C:
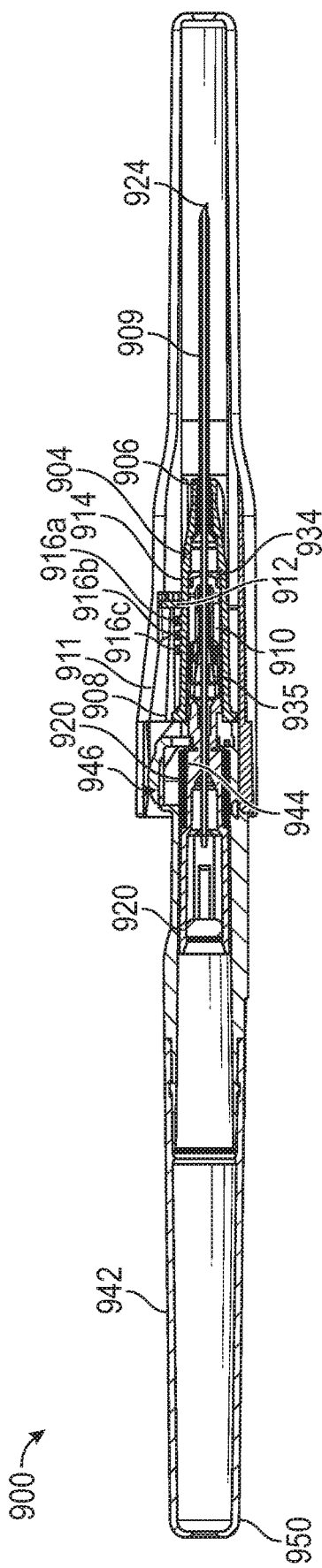
FIG. 9C is a cross-sectional view of the catheter system of FIG. 9A, according to some embodiments.
Figure 9D:
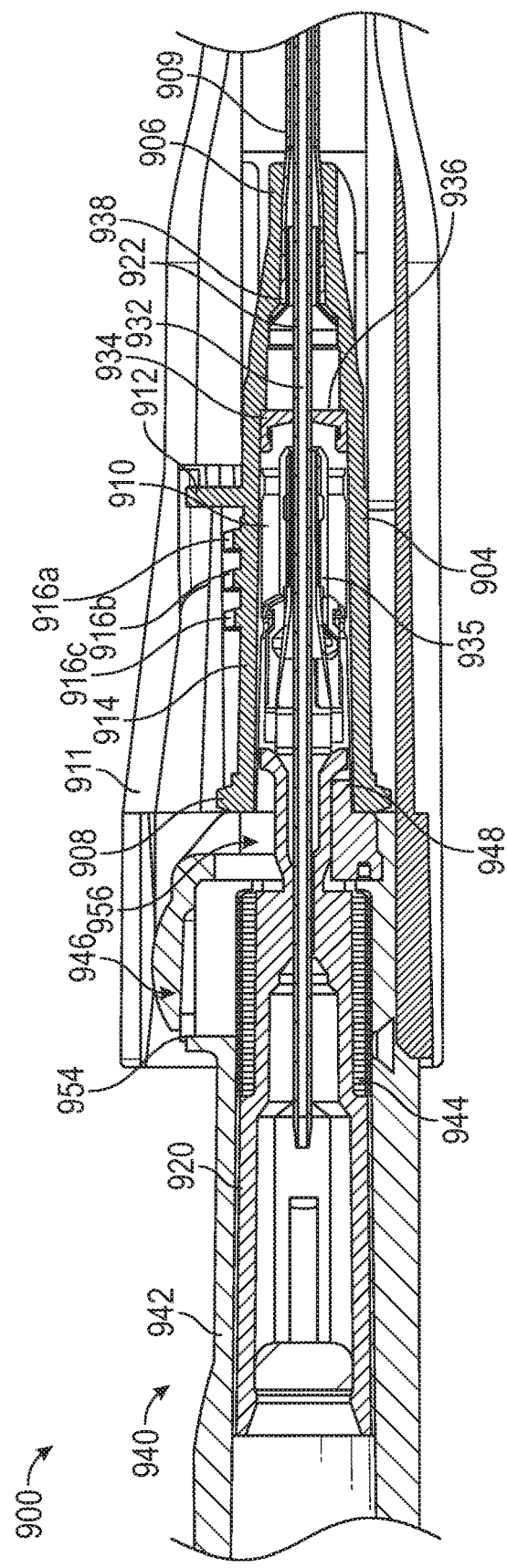
FIG. 9D is an enlarged cross-sectional view of the catheter system of FIG. 9A, according to some embodiments.
Figure 9E:
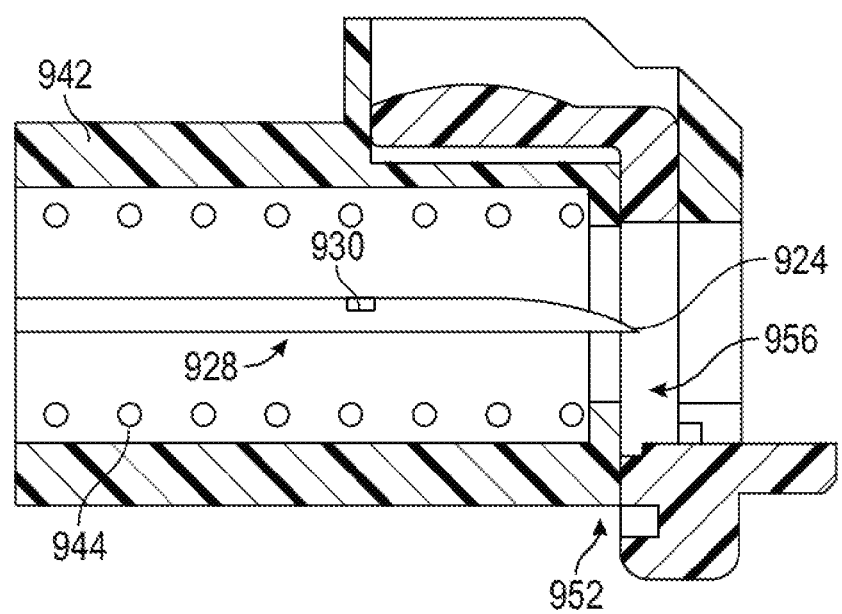
FIG. 9E is a cross-sectional view of the catheter system of FIG. 9A, illustrating the catheter hub advanced distally with respect to the needle hub and an example spring activated, according to some embodiments.
Figure 9F:
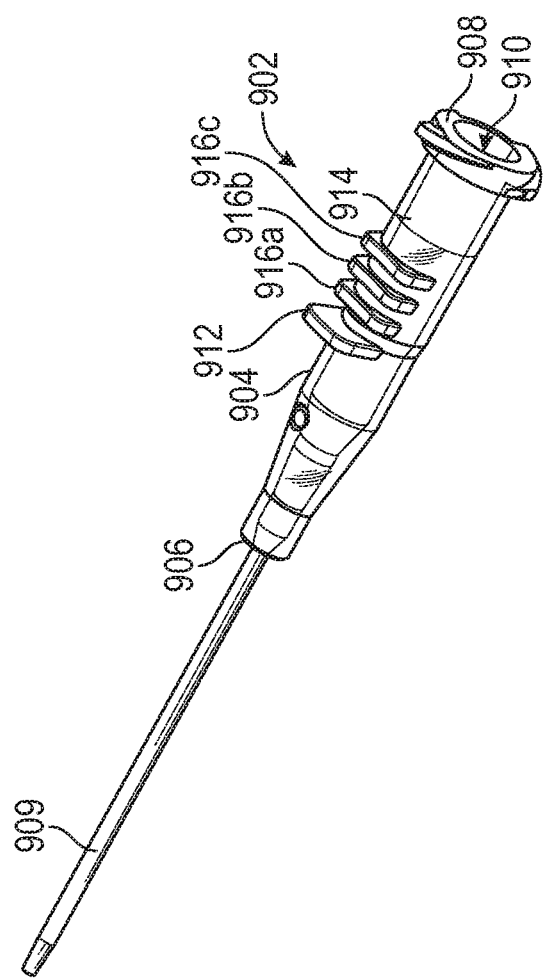
FIG. 9F is an upper perspective view of the catheter hub of the catheter system of FIG. 9A, according to some embodiments.
Figure 9G:
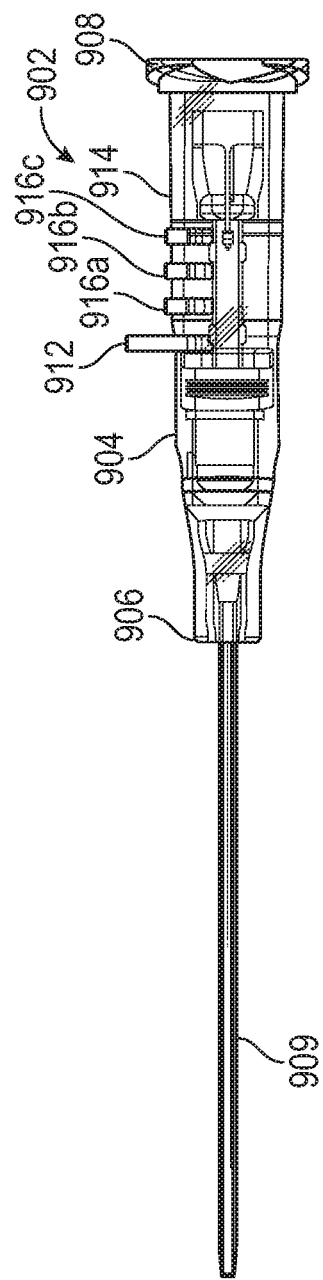
FIG. 9G is a side view of the catheter hub of the catheter system of FIG. 9A, according to some embodiments.
Figure 9H:
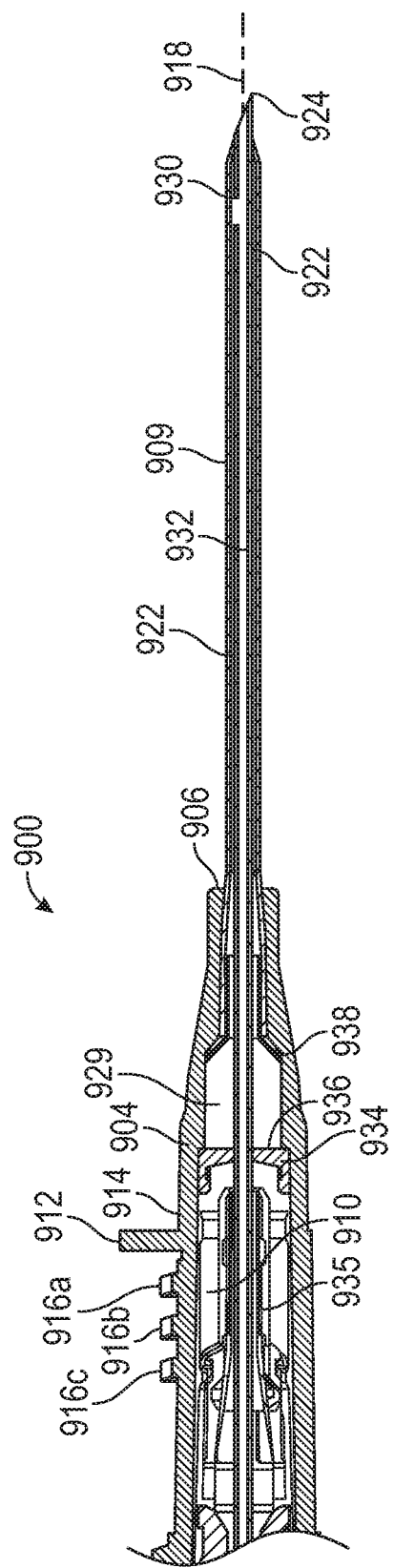
FIG. 9H is a cross-sectional view of a distal portion of the catheter system of FIG. 9A, according to some embodiments.

In some embodiments, the ribs 916 may be configured to resist rotation of the catheter hub 904 with respect to the barrel 942 in response to distal advancement of the catheter hub 904 with respect to the barrel 942 and removal of the projection 948 from the distal end 952 of the barrel 942. FIG. 9B illustrates distal advancement of the catheter hub 904 with respect to the barrel 942 prior to activation of the activation latch 946. In some embodiments, the user may distally advance the catheter hub 904 once the user observes blood within the flashback chamber 929. In some embodiments, the finger of the user may be placed against the ribs 916 and/or the push tabs 912 to distally advance the catheter hub 904 and to resist rotation of the catheter hub 904. In some embodiments, the catheter system 900 and/or the catheter hub 904 may be contacted by the user only at the push tab 912 and the ribs 916. Thus, in some embodiments, the configuration of the push tab 912 and the ribs 916 is important for tactile response and rotational control.

In some embodiments, after the catheter hub 904 is distally advanced, the user may depress the activation latch 946, which may retract the introducer needle 922 into the barrel 942, where the introducer needle 922 may be fully encapsulated. In some embodiments, the activation latch 946 may be depressed by a particular finger of a first hand of the user while a particular finger of a second hand of the user is positioned on the ribs 916 and/or the push tab 912 to stabilize and prevent movement of the catheter hub 903. In some embodiments, after the introducer needle 922 is withdrawn, the septum 934 may close to prevent blood from leaking from the proximal end 908 of the catheter hub 904.

In some embodiments, the activation latch 946 may be disposed proximal to the flashback chamber 929 and/or the ribs 916 and the push tab 912 may be disposed between the activation latch 946 and the flashback chamber 929. Thus, in some embodiments, a location of the ribs 916, the push tab 912, and the activation latch 946 with respect to the flashback chamber 929 may enable the user to place fingers of the user on one or more of the ribs 916, the push tab 912, and the activation latch 946 without obstructing the user's view of the flashback chamber 929 beneath the fingers.

Figure 10C:
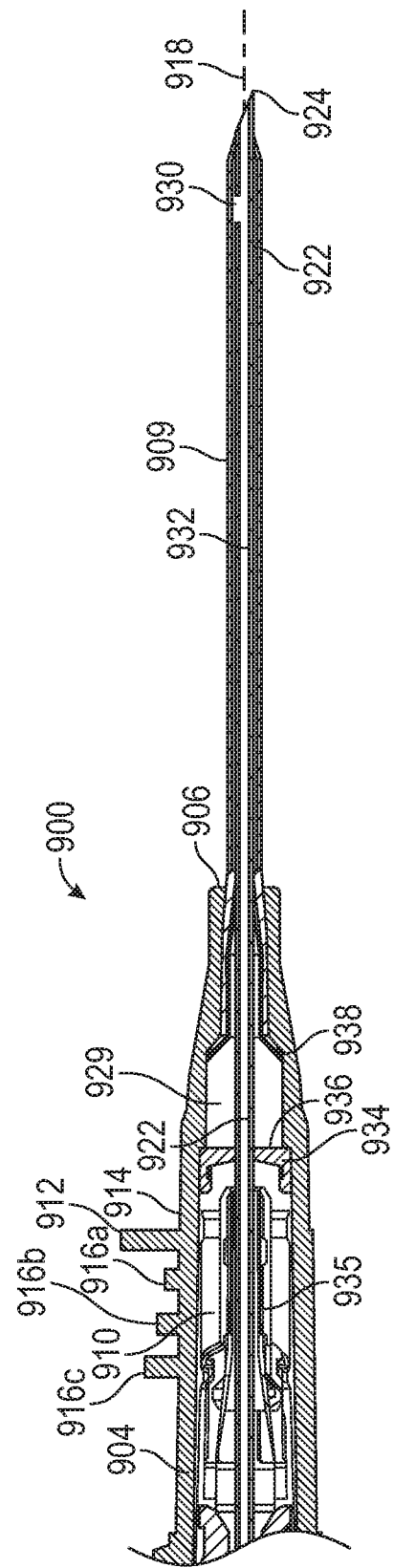
FIG. 10C is a cross-sectional view of the catheter hub of FIG. 10A coupled to the needle hub of FIG. 9A, according to some embodiments.

Referring now to FIG. 10, in some embodiments, the first rib 916a may be shorter in height than the second rib 916b. In some embodiments, the second rib 916b may be shorter in height than the third rib 916c. In some embodiments, an upper surface of the first rib 916a, an upper surface of the second rib 916b, and an upper surface of the third rib 916c may be angled upwardly in a proximal direction, as illustrated, for example, in FIG. 10A. In some embodiments, an angle of the upper surface of the third rib 916c may be greater than an angle of the upper surface of the second rib 916b, which may be greater than an angle of the upper surface of the first rib 916a. In these embodiments, the first rib 916a, the second rib 916b, and the third rib 916c may be configured to mirror a contour of the finger of the user.

Figure 11A:
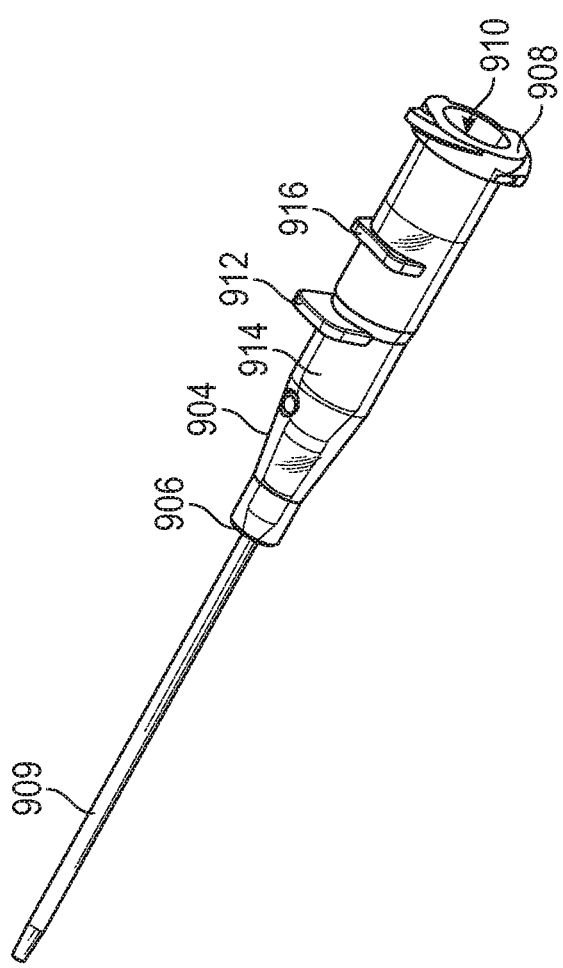
FIG. 11A is an upper perspective view of another catheter hub, according to some embodiments.
Figure 11B:
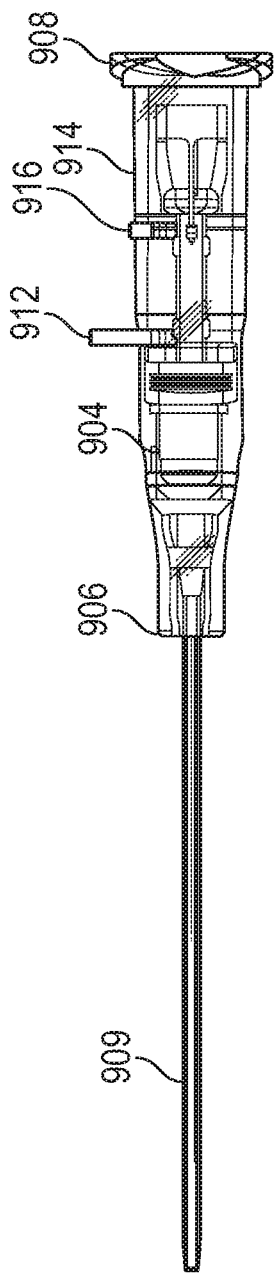
FIG. 11B is a side view of the catheter hub of FIG. 11A, according to some embodiments.
Figure 11C:
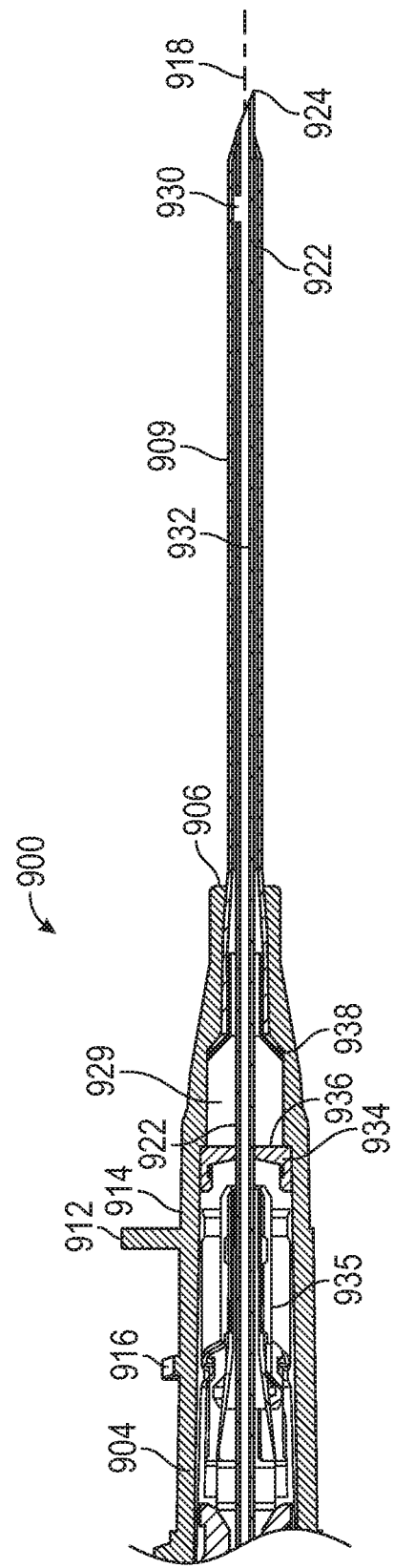
FIG. 11C is a cross-sectional view of the catheter hub of FIG. 11A coupled to the needle hub of FIG. 9A, according to some embodiments.

Referring now to FIG. 11, in some embodiments, the catheter hub 904 may include just one rib 916, which may extend outwardly from the upper surface 914 of the catheter hub 904. In some embodiments, the rib 916 may be proximal to the push tab 912. In some embodiments, the rib 916 may be shorter in height than the push tab 912. In some embodiments, the rib 916 may be generally perpendicular to the longitudinal axis 918 of the catheter tube 909. In some embodiments, a distance between the rib 916 and the push tab 912 may be half or less than half of a distance between the push tab 912 and the distal end 906 of the catheter hub 904, which may facilitate simultaneous contact between the push tab 912 and the rib 916. In some embodiments, a space between the push tab 912 and the rib 916 may facilitate support of a substantial portion of the finger of the user, which may allow the user more control over the catheter hub 904.

In some embodiments, the rib 916 may enhance stability during insertion of the catheter system 900 into vasculature of a patient and may resist angular rotation of the catheter hub 904. In some embodiments, the rib 916 may cradle the finger of the user as the push tab 912 is advanced distally. In some embodiments, the flashback chamber 929 may be disposed distal to the rib 916 and the push tab 912, which may improve visualization of the flashback chamber 929 by the user. Further, in some embodiments, the rib 916 may be configured to resist rotation of the catheter hub 904 with respect to the barrel 942 in response to distal advancement of the catheter hub 904 with respect to the barrel 942 and removal of the projection 948 from the distal end 952 of the barrel 942.

Figure 12:
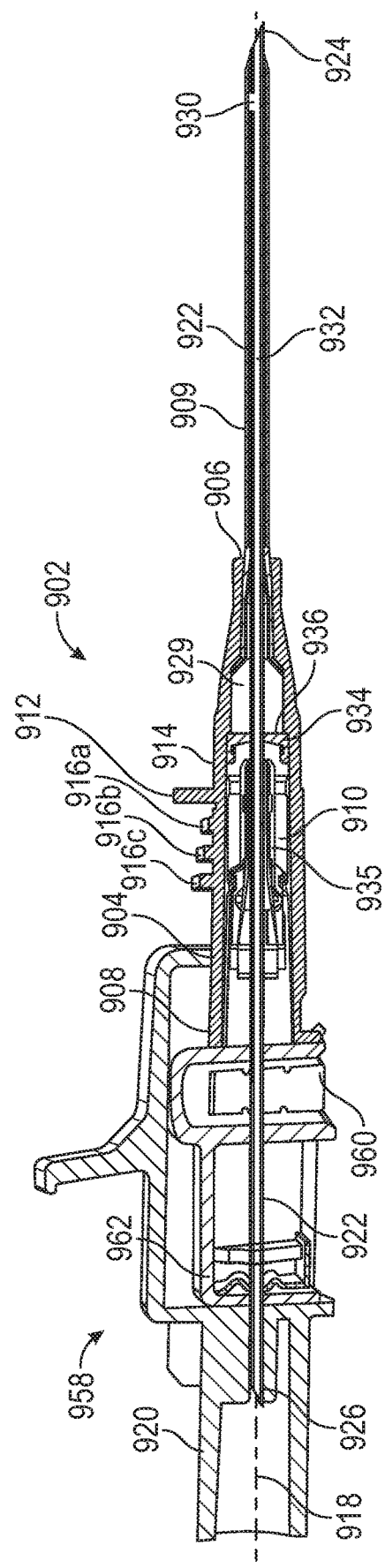
FIG. 12 is a cross-sectional view of another catheter system, according to some embodiments.

Referring now to FIG. 12, in some embodiments, the safety feature of the catheter system 900 may be passive. In some embodiments, a safety feature 958 is an example of a possible passive safety feature of the catheter system 900. In some embodiments, the safety feature 958 may be configured to shield the sharp distal tip 924 of the introducer needle 922 in response to proximal withdrawal of the needle hub 920 with respect to the catheter hub 904. A similar mechanism may occur in any number of suitable passive safety features that may be included in the catheter system 900. In some embodiments, the ribs 916 may be configured to resist rotation of the catheter hub 904 with respect to the needle hub 920 in response to proximal withdrawal of the needle hub 920 with respect to the catheter hub 904.

In some embodiments, the safety feature 958 may include a safety clip 960, which may be positioned within a needle shield 962 to block and prevent the sharp distal tip 924 from exiting the needle shield 962 once the sharp distal tip 924 has been drawn proximally past the safety clip 960. Thus, in some embodiments, the sharp distal tip 924 may be trapped within the needle shield 962. In some embodiments, the needle hub 920 may be slidable proximally with respect to the needle shield 962.

In some embodiments, the safety clip 960 may be configured to securely retain the connection between needle shield 962 and the proximal end 908 of the catheter hub 904. In some embodiments, the safety clip 960 further comprises a pawl or other feature that selectively and/or temporarily interconnects with a surface of the proximal end 908 when the safety clip 960 is held in a first position. In some embodiments, the first position of the safety clip 960 may be maintained by contact between the introducer needle 922 and the safety clip 960. In some embodiments, when the introducer needle 922 is withdrawn past the safety clip 960 in a proximal direction, the safety clip 960 may be released from the first position and may be repositioned to block the sharp distal tip 924 from exiting the needle shield 962 distally. In some embodiments, when the safety clip 960 is repositioned, the pawl or other feature releases the surface of proximal end 908, thereby permitting physical separation of the catheter hub 904 from the needle shield 962.

It is understood that the catheter system 900 may include any suitable active or passive safety mechanisms. In some embodiments, the safety feature may include an internal interlock in which the safety feature is coupled with an internal surface of the catheter hub 904. Non-limiting examples of safety features that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety.

In some embodiments, the safety feature may include an external interlock in which the safety feature is coupled with an external surface of the catheter hub 904. Non-limiting examples of safety features that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety.

In some embodiments, the safety feature may include a clip disposed within the catheter hub 904, a non-limiting example of which is provided in U.S. Pat. No. 6,117,108, titled SPRING CLIP SAFETY IV CATHETER, filed Jun. 12, 1998, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the V-clip may selectively retain a portion of the catheter hub 904.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

What is claimed is:

1. A catheter system, comprising:
   a catheter assembly, comprising:
      a catheter hub, comprising a distal end, a proximal end, a lumen disposed between the distal end and the proximal end, a push tab extending outwardly from an upper surface of the catheter hub, a first rib, a second rib proximal to the first rib, and a third rib proximal to the second rib, wherein the first rib, the second rib, and the third rib are shorter in height than the push tab, proximal to the push tab, and extend outwardly from the upper surface of the catheter hub;
      a septum disposed within the lumen of the catheter hub; and
      a catheter tube extending distally from the distal end of the catheter hub;
   a needle hub;
   an introducer needle secured within the needle hub and extending through the catheter tube, wherein the introducer needle comprises a flashback notch, wherein the catheter system is configured such that in response to insertion of the introducer needle into vasculature, blood flows into the introducer needle, through the flashback notch, between an outer surface of the introducer needle and an inner surface of the catheter tube, and into a flashback chamber disposed between a distal face of the septum and a proximal end of the catheter tube, wherein the flashback chamber is disposed distal to the first rib, the second rib, the third rib, and the push tab.

2. The catheter system of claim 1, further comprising:
   a barrel comprising a proximal end and a distal end, wherein the needle hub is slidably disposed in the barrel, wherein the barrel is generally hollow;
   a spring disposed about the introducer needle;
   an activation latch having a top and a bottom and movably mounted adjacent to the distal end of the barrel and adapted for selective engagement with the needle hub to hold the needle hub adjacent to the distal end of the barrel against the bias of the spring such that the introducer needle extends beyond the distal end of the barrel and through the catheter tube with the catheter hub adjacent to the distal end of the barrel; and
   a projection extending from the activation latch for engagement with the catheter hub to prevent movement of the activation latch when the catheter hub is adjacent to the distal end of the barrel, wherein the first rib, the second rib, and the third rib are configured to resist rotation of the catheter hub with respect to the barrel in response to distal advancement of the catheter hub with respect to the barrel and removal of the projection from the distal end of the barrel.

3. The catheter system of claim 2, wherein the activation latch is disposed proximal to the flashback chamber.

4. The catheter system of claim 2, wherein the push tab, the first rib, the second rib, and the third rib are disposed between the activation latch and the flashback chamber.

5. The catheter system of claim 1, wherein the first rib, the second rib, and the third rib are generally parallel to each other.

6. The catheter system of claim 1, wherein the first rib, the second rib, and the third rib are a same height.

7. The catheter system of claim 1, wherein the push tab, the first rib, the second rib, and the third rib are evenly spaced apart.

8. The catheter system of claim 1, wherein the first rib, the second rib, and the third rib form a cradle shape.

9. The catheter system of claim 1, wherein the first rib, the second rib, the third rib, and the push tab are generally perpendicular to a longitudinal axis of the catheter tube.

10. The catheter system of claim 1, wherein the first rib is shorter in height than the second rib, wherein the second rib is shorter in height than the third rib.

11. The catheter system of claim 1, further comprising a passive safety feature configured to shield a distal tip of the introducer needle in response to proximal withdrawal of the needle hub with respect to the catheter hub, wherein the first rib, the second rib, and the third rib are configured to resist rotation of the catheter hub with respect to the needle hub in response to proximal withdrawal of the needle hub with respect to the catheter hub.

12. A catheter system, comprising:
 a catheter assembly, comprising:
  a catheter hub, comprising a distal end, a proximal end, a lumen disposed between the distal end and the proximal end, a push tab extending outwardly from an upper surface of the catheter hub and a rib, wherein the rib is shorter in height than the push tab, proximal to the push tab, generally parallel to the push tab, and extends outwardly from the upper surface of the catheter hub;
  a septum disposed within the lumen of the catheter hub; and
  a catheter tube extending distally from the distal end of the catheter hub;
 a needle hub;
 an introducer needle secured within the needle hub and extending through the catheter tube, wherein the introducer needle comprises a flashback notch, wherein the catheter system is configured such that in response to insertion of the introducer needle into vasculature, blood flows into the introducer needle, through the flashback notch, between an outer surface of the introducer needle and an inner surface of the catheter tube, and into a flashback chamber disposed between a distal face of the septum and a proximal end of the catheter tube, wherein the flashback chamber is disposed distal to the rib and the push tab.

13. The catheter system of claim 12, further comprising:
 a barrel comprising a proximal end and a distal end, wherein the needle hub is slidably disposed in the barrel, wherein the barrel is generally hollow;
 a spring disposed about the introducer needle;
 an activation latch having a top and a bottom and movably mounted adjacent to the distal end of the barrel and adapted for selective engagement with the needle hub to hold the needle hub adjacent to the distal end of the barrel against the bias of the spring such that the introducer needle extends beyond the distal end of the barrel and through the catheter tube with the catheter hub adjacent to the distal end of the barrel; and
 a projection extending from the activation latch for engagement with the catheter hub to prevent movement of the activation latch when the catheter hub is adjacent to the distal end of the barrel, wherein the rib is configured to resist rotation of the catheter hub with respect to the barrel in response to distal advancement of the catheter hub with respect to the barrel and removal of the projection from the distal end of the barrel.

14. The catheter system of claim 13, wherein the activation latch is disposed proximal to the flashback chamber.

15. The catheter system of claim 13, wherein the push tab and the rib are disposed between the activation latch and the flashback chamber.

16. The catheter system of claim 12, wherein a distance between the rib and the push tab is half or less than half of a distance between the push tab and the distal end of the catheter hub.

17. The catheter system of claim 12, further comprising a passive safety feature configured to shield a distal tip of the introducer needle in response to proximal withdrawal of the needle hub with respect to the catheter hub, wherein the rib is configured to resist rotation of the catheter hub with respect to the needle hub in response to proximal withdrawal of the needle hub with respect to the catheter hub.

18. A catheter system, comprising:
 a catheter assembly, comprising:
  a catheter hub, comprising a distal end, a proximal end, a lumen disposed between the distal end and the proximal end, a push tab extending outwardly from an upper surface of the catheter hub, a first rib, a second rib proximal to the first rib, and a third rib proximal to the second rib, wherein the first rib, the second rib, and the third rib are shorter in height than the push tab, proximal to the push tab, and extend outwardly from the upper surface of the catheter hub, wherein an upper surface of the first rib, an upper surface of the second rib, and an upper surface of the third rib are angled upwardly in a proximal direction;
  a septum disposed within the lumen of the catheter hub; and
  a catheter tube extending distally from the distal end of the catheter hub;
 a needle hub;
 an introducer needle secured within the needle hub and extending through the catheter tube, wherein the introducer needle comprises a flashback notch, wherein the catheter system is configured such that in response to insertion of the introducer needle into vasculature, blood flows into the introducer needle, through the flashback notch, between an outer surface of the introducer needle and an inner surface of the catheter tube, and into a flashback chamber disposed between a distal face of the septum and a proximal end of the catheter tube.

19. The catheter system of claim 18, further comprising:
 a barrel comprising a proximal end and a distal end, wherein the needle hub is slidably disposed in the barrel, wherein the barrel is generally hollow;

a spring disposed about the introducer needle;

an activation latch having a top and a bottom and movably mounted adjacent to the distal end of the barrel and adapted for selective engagement with the needle hub to hold the needle hub adjacent to the distal end of the barrel against the bias of the spring such that the introducer needle extends beyond the distal end of the barrel and through the catheter tube with the catheter hub adjacent to the distal end of the barrel; and a projection extending from the activation latch for engagement with the catheter hub to prevent movement of the activation latch when the catheter hub is adjacent to the distal end of the barrel, wherein the first rib, the second rib, and the third rib are configured to resist rotation of the catheter hub with respect to the barrel in response to distal advancement of the catheter hub with respect to the barrel and removal of the projection from the distal end of the barrel.

20. The catheter system of claim 19, wherein the activation latch is disposed proximal to the flashback chamber.

* * * * *